(12) United States Patent
Venge

(10) Patent No.: US 7,405,047 B2
(45) Date of Patent: Jul. 29, 2008

(54) METHOD FOR ESTIMATION OF THE AMOUNT OF SPECIFIC CELL TYPES

(75) Inventor: Per Venge, Uppsala (SE)

(73) Assignee: Phadia AB, Uppsala (SE)

( * ) Notice: Subject to any disclaimer, the term of this patent is extended or adjusted under 35 U.S.C. 154(b) by 504 days.

(21) Appl. No.: 10/178,211

(22) Filed: Jun. 24, 2002

(65) Prior Publication Data
US 2003/0077666 A1 Apr. 24, 2003

Related U.S. Application Data

(60) Provisional application No. 60/300,759, filed on Jun. 25, 2001.

(30) Foreign Application Priority Data

Jun. 25, 2001 (SE) .................... 0102220

(51) Int. Cl.
*G01N 33/53* (2006.01)

(52) U.S. Cl. .............. 435/7.1; 435/7.23; 435/7.24; 435/287.2; 436/517; 436/17; 436/172; 436/175; 436/177

(58) Field of Classification Search .......... 435/2, 435/7.1, 7.2, 7.23, 7.24, 7.92, 326, 332, 372.2, 435/372.3, 287.2; 436/517, 519, 10, 17, 436/63, 64, 172, 175, 177
See application file for complete search history.

(56) References Cited

U.S. PATENT DOCUMENTS 5,426,029 A * 6/1995 Rittershaus et al. ......... 435/7.21

5,747,265 A * 5/1998 Parsons et al. ............... 435/7.2

FOREIGN PATENT DOCUMENTS

AU 756780 * 10/2000 .................. 435/7.2

OTHER PUBLICATIONS

Moshfegh et al., Methods of Simultaneous Quantitative Analysis of Eosinophil and Neutrophil Adhesion and Transmigration, Scand. J. Immunol. 50: 262-269 (1999).*
Carlson et al., Human Eosinophil Peroxidase: purification and characterization (The Journal of Immunology, 134 (3): 1875-1879 (Mar. 1985).*
McEuen et al., Mass, charge, and subcellular localization of a unique secretory product identified by the basophil-specific antibody BB1 (J. Allergy Clin Immunol, 107 : 842-848 (May 2001).*
Cella et al., Platelet factor 4 (PF4) and heparin released platelet factor 4 (HR-PF4) in diabetes mellitus. Effect of the duration of the disease. Folia haematologica (Leipzig, Germany:1928), 113 (5): 646-654 (1986) (Abstract).*
Xu et al. The development of an assay for human neutrophil lipocalin (HNL) to be used as a specific marker of neutrophil activity in vivo and vitro, Journal of Immunological Methods 171: 245-252 (1994).*

(Continued)

*Primary Examiner*—Gailene R Gabel
(74) *Attorney, Agent, or Firm*—Porter Wright Morris & Arthur LLP

(57) ABSTRACT

The present invention relates to the estimation of the amount of subtypes of specific cells, for example the number of certain subtypes of leukocytes, by measurements of unique proteins in extracts of blood and other biological material. The knowledge of the number or amount of specific subtypes of white cells is important in the clinical diagnosis and surveillance of subjects with inflammatory disease including infectious disease, cancer, allergy/asthma etc.

20 Claims, 3 Drawing Sheets

OTHER PUBLICATIONS

McEuen et al., Dev't and characterization of a MAb specific for human basophils and the identification of a unique secretory product of basophil activation, Laboratory Investigation, 79 (1): 27-38 (Jan. 1999).*

Cella et al., Platelet factor 4 (PF4) and heparin released platelet factor 4 (HR-PF4) in diabetes mellitus. Effect of the duration of the disease. Folia haematologica (Leipzig, Germany:1928), 113 (5): 646-654 (1986).*

Venge et al, *Immunology*, 50:19-26 (1983).

Peterson et al, *Eur. J. Haematol.*, 40:415-423 (1988).

Olofsson et al, *Scand. J. Haematol.*, 18:73-80 (1977).

Ouchterlony, *State Bacteriology Laboratory*, Stockholm, vol. XXVI, 4:508-519 (1949).

Olsson et al, *Scand. J. Haemat.*, 9:483-491 (1972).

Klempner et al, *The Journal of Cell Biology*, 86:21-28 (1980).

Agner, *Acta Chem. Scand.*, 12(1):89-94 (1958).

Carlson et al, *The Journal of Immunology*, 134(3):1875-1879 (1985).

Cooray et al, *Veterinary Immunology and Immunopathology*, 38:261-272 (1993).

Xu et al, *Journal of Immunological Methods*, 171:245-252 (1994).

Xu et al, *Scand. J. Clin. Lab. Invest.*, 54:365-376 (1994).

Borregaard et al, *The Journal of Cell Biology*, 97:52-61 (1983).

Reiter, *Int. J. Tiss. Reac.*, 1:87-96 (1983).

Galfre et al, *Nature*, 266:550-552 (1977).

Nielsen et al, *Allergy*, 53:778-785 (1998).

* cited by examiner

METHOD FOR ESTIMATION OF THE AMOUNT OF SPECIFIC CELL TYPES

RELATED APPLICATION

The present application claims priority under 35 U.S.C. §119 of U.S. application Ser. No. 60/300,759 filed Jun. 25, 2001.

FIELD OF THE INVENTION

The present invention relates to the estimation of the amount of subtypes of specific cells, for example the number of certain subtypes of leukocytes, by measurements of unique proteins in extracts of blood and other biological material. The knowledge of the number or amount of specific subtypes of white cells is important in the clinical diagnosis and surveillance of subjects with inflammatory disease including infectious disease, cancer, allergy/asthma etc.

BACKGROUND OF THE INVENTION

The estimation of the number of various leukocytes in blood and other body fluids is one of the most widely used tools in medicine. The traditional way of obtaining this information is the counting and differentiating of the cells under the light microscope. This technique is complemented by the automated counting in cell counters based on the principle of counting the number of particles in the fluid and the measurement of various physical parameters such as size, forward and side scatter, but also my histochemical staining of cells. An extension of these techniques is the flow cytometer principle in which antibodies are used to identify individual cells based on their cell surface antigens or by means of their content of intracellular antigens after permeabilisation of the cells.

In WO 00/58726 there is described a method for quantitating leukocyte count in whole blood. However, this method does not quantitate different specific subtypes of leukocytes in respect of number or ratio.

SUMMARY OF THE INVENTION

There exists a need of easy-to-use, inexpensive and reliable tests to estimate the number of various white bloods cells such as neutrophils and eosinophils, in blood and other body fluids, applicable in the point-of-care situation, thus supporting the medical doctor in his/hers immediate decision-making.

The present inventor has found that the extraction of whole blood with for example detergents such as CTAB (N-cetyl-N,N,N-trimethylammonium bromide), and the subsequent measurement by specific immunoassays of the neutrophil proteins, MPO (myeloperoxidase), HNL (human neutrophil lipocalin) or lactoferrin, or the specific measurements of eosinophil proteins such as EPX (eosinophil protein x) or EPO (eosinophil peroxidase), will accurately identify the number of neutrophils or eosinophils present in the blood. The estimation of the numbers of neutrophils is useful in the diagnosis and monitoring of subjects with inflammatory diseases such as infections, rheumatoid diseases, but also in conjunction with medical treatment, in particular cytostatic treatment, where the reduced production of neutrophils i.e. neutropenia, may occur as a serious adverse effect of treatment. The estimation of eosinophil numbers is useful in patients with allergic disease, chronic inflammatory diseases, parasitic disease, certain cancers such as Hodgkin's disease, but also as a general indicator of disease, since elevated numbers of eosinophils may occur in a number of diseases for unknown reasons.

In the broadest sense the invention means that the number of any given cell population in a body fluid may be possible to estimate, given the availability of immunoassays for molecules that are unique for the cell population to be estimated. Thus, the invention could be adopted to the estimation of lymphocyte populations in e.g. patients with HIV-infections, cancer, autoimmune disease, but also for the estimation of populations at various maturation stages of myeloid cells, since some intracellular proteins are produced primarily by immature cells and other proteins primarily by more mature cells.

Thus, the invention relates to a method to in vitro estimate the amount, wherein the amount refers to either the number or ratio of specific cell subtypes in a patient sample, comprising a) extracting an aliquot of said sample; and b) measuring the concentration of cell specific molecule(s) in said extracted sample.

The specific cell subtypes may be subtypes of leukocytes.

The cell specific molecules may for example be extra- and intracellular proteins or antigens, cell surface markers etc.

The sample is preferably blood or other body fluid. A very small amount of sample is extracted, such as 1-10 µl of sample but larger volumes might be considered.

The extraction is preferably with cationic detergent. The extraction time is very short, for example 1 minute. Preferably, the detergent is CTAB.

Preferably, the measuring in step b) is by an immunoassay, such as ELISA (enzyme-linked immunosorbent assay), EIA (enzyme immunoassay), FEIA (fluoroenzyme immunoassay), or RIA (radio immunoassay).

In the method of the invention, the said concentration of said cell specific molecule(s) may be correlated with the number of the respective cell type(s).

In one embodiment, two cell specific molecules are measured in step b) and a ratio between the concentrations of said molecules is determined.

The cell specific molecule(s) may be a neutrophil protein, such as MPO (myeloperoxidase), HNL (human neutrophil lipocalin) or lactoferrin for measuring neutrophils.

The cell specific molecule may also be an eosinophil protein, such as EPX (eosinophil protein x), EPO (eosinophil peroxidase) for measuring eosinophils.

Alternatively, the cell specific molecule is/are a basophil protein, such as BB 1, or a thrombocytic protein, such as β-thromboglobulin, for measuring thrombocytes.

In another alternative the cell specific molecule is/are cell surface markers such as CD20 for measuring B-lymphocytes and CD3 T-lymphocytes or CD4 and CD8 for measuring different lymphocyte populations.

In a further alternative, the cell specific molecule is/are CD14 or lysozyme for measuring monocytes.

DETAILED DESCRIPTION OF THE INVENTION

The present invention will be described more closely below in association with the accompanying drawings in which FIG. 1 shows a correlation between the number of blood neutrophils and the concentration of MPO protein in detergent extracted whole blood.

EXPERIMENTAL SECTION

Figure 1:
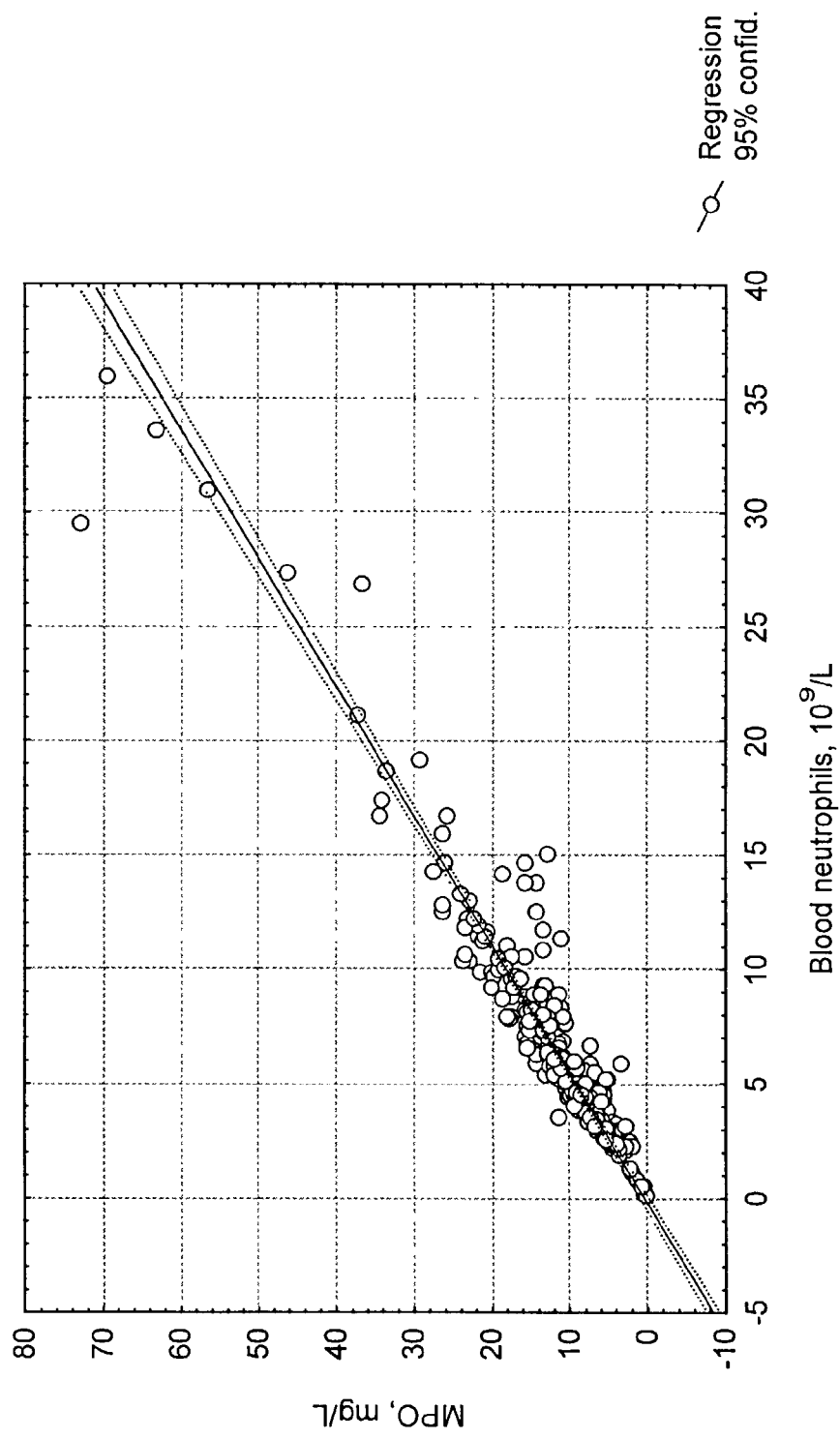

Isolation and Purification of Human Neutrophil and Eosinophil Granule Proteins Granules were prepared from the buffy coat of granulocytes obtained from healthy blood donors using a modification of the procedure described by Peterson et al (Eur. J. Haematol. 40 (1988) 415-423). In brief, the red blood cells were allowed to sediment using Dextran T-500 before collection of the leukocyte rich plasma. Leucocytes were washed twice in 0.34 M Sucrose and the suspended in 5 volumes of 0.34 M Sucrose. The leukocytes were cavitated using $N_2$ at a pressure of 750 psi for 30 min at +4° C. (Klempner et al., J. Cell. Biol. 86 (1980) 21-28; and Borregaard et al., J. Cell. Biol. 97 (1983) 52-61). The cavitate was suspended in 0.34 M Sucrose, 0.17 M NaCl and centrifuged for 20 min at 450×g at +4° C.

The supernatant was centrifuged for 20 min at 10,000×g at +4° C. to sediment the granules. Myeloperoxidase (MPO) was purified from granule extracts according Olsson et al (Scand. J. Haematol. 9 (1972) 483-491) and Cooray et al (Vet. Immunol. Immunopathol. 38 (1993) 261-272). The final preparation was completely homogenous according to the absorbance ratio A430 nm/A280 m which was 0.80 (Agner Acta. Chem. Scand. 12 (1958) 89-94. Human neutrophil lipocalin (HNL) was purified as described (Xu et al., Scand J Clin Lab Invest 54 (1994) 365-376. HNL was purified to homogeneity according SDS-PAGE electrophoresis and silver staining and the antigen did not react with antibodies against the other neutrophil proteins, MPO; Lactoferrin, Cathepsin G, Elastase and Lysozyme. Lactoferrin was purified as described (Reiter Int. J. Tissue React. 5 (1983) 87-96. Eosinophil Peroxidase (EPO) was purified as described (Carlson et al J. Immunol. 134 (1985) 1875-1879) and the final preparation was homogenous according to the absorbance ratio A415 nm/A280 nm that was 1.15.

Eosinophil protein (EPX) was purified to homogeneity as described (Peterson et al., Immunol. 50 (1983) 19-26. The final preparation appeared as one band on SDS-PAGE electrophoresis and did not react with antibodies against eosinophil cationic protein (ECP), elastase, cathepsin G, MPO and EPO.

Production of Antibodies

Polyclonal Antibodies

Antibodies against MPO, HNL, EPO and EPX was raised in rabbits by multiple site intracutaneous injections into the rabbits of total 50-100 μg of the purified proteins suspended in Freund's complete and incomplete adjuvant. The specificity of the antibodies was evaluated by double immuno diffusion (Ouchterlony Acta Pathol. Microbiol. Scand 26 (1949) 507-) in agarose and tested against extracts of neutrophils and eosinophil granules and the following purified proteins: cathepsin G, elastase, MPO, lysozyme, lactoferrin, ECP, EPX; EPO.

Monoclonal Antibodies

Female Balb/c mice were immunized subcutaneously with purified protein. Priming was done by injecting 50 μg of pure protein mixed with Freund's complete adjuvant. Three boosters were done with approximately 50 μg of pure protein in PBS (phosphate buffered saline). Spleen cells were fused as described (Galfré et al., Nature 266 (1977) 550-552) with Sp2/0 myeloma cells. Supernatants from the cell cultures were screened for antibodies using ELISA technique with antigen-coated wells. Antibodies in supernatants were also screened for specificity to respective granule protein and mapped for epitopes in BIAcore® (BIAcore, Uppsala, Sweden). Hybridomas were selected according to the ELISA and BIAcore experiments and cloned, expanded and purified. All selected antibodies were of IgGI subtype.

Immunoassays

HNL was assessed using a radioimmunoassay as described (Xu et al., J. Immunol. Methods 171 (1994) 245-252. Inter- and intra assay variations were less than 10% and detection limit was less than 4 μg/l.

EPX and Myeloperoxidase was measured using commercially available radioimmunoassays (Pharmacia Diagnostics AB, Uppsala, Sweden). Inter- and intra assay variations were less than 10% and detection limit was less than 3 and 8 μg/l, respectively EPO was measured using a protype immunofluorometric assay utilising the Pharmacia CAP system® as described (Nielsen et al., Allergy 53 (1998) 778-785. Inter- and intra assay variations were less than 8% and detection limit was less than 0.5 μg/l. Lactoferrin was estimated as described (Olofsson et al., Scand J Haematol 18 (1977) 73-80). Inter- and intra assay variations were less than 8% and detection limit was less than 2 μg/l.

Blood Samples

EDTA-containing blood samples drawn from patients were randomly collected at the University Hospital, Uppsala, Sweden. Blood cell counts were performed on each sample by means of a Coulter STKS (Beckman Coulter, Inc.) cell counter.

Granule proteins were extracted from granulocytes by means of adding CTAB (N-cetyl-N,N,N-trimethyl-ammonium bromide) at a final concentration of 0.05-0.5% to a small aliquot of blood, 1-10 μl. The mixture was then incubated for at least 1 minute and then stored frozen at −20° C. before analysis.

Statistical Evaluation

Regression analysis was performed using the statistical package, Statistica (Statsoft, Tulsa, USA).

EXAMPLE 1

Estimation of the Number of Blood Neutrophils

The present invention shows that extraction of a small aliquot of blood, 1-10 μl, with CTAB, final concentration 0.05-0.5%, for at least 1 minute and subsequent measurement of the neutrophil protein MPO by means of a specific immunoassay accurately estimates the numbers of neutrophils in the blood.

As shown in FIG. 1, the concentration of MPO in the extract was significantly and linearly correlated (r=0.96) to the number of neutrophils in the extracted blood as estimated by means of a Coulter STKS (Beckman Coulter, Inc.) cell counter. From the equation of the regression line it is apparent that the deviation from origo was minimal, indicating the cell specificity of the measurement. The results were obtained from a mixed population of hospitalized patients (n=275) having both elevated and reduced levels of neutrophils in the their blood. Thus, some patients had highly elevated levels due to acute bacterial infections and others had seriously reduced levels due to leukemia or cytostatic drug treatment. In spite of the inclusion of these extremes in the calculation, the relationship between number of neutrophils and the concentration of MPO was linear over the entire range measured. When HNL was measured the corresponding correlation was r=0.93 and also with a linear relationship to the number of neutrophils over the entire range. Lactoferrin measurement also showed a linear relationship over the entire range and a correlation coefficient of r=0.82.

EXAMPLE 2

Estimation of the Degree of Maturation of the Neutrophil Population

It is well known that MPO is stored in the primary granules of neutrophils, whereas lactoferrin and HNL are stored in secondary granules. This is because the production of MPO primarily takes place during the early maturation steps i.e. by myeloblasts and promyelocytes, whereas lactoferrin and HNL primarily are produced during later maturation steps i.e. by myelocytes. It is also known that production of MPO is less affected by an increased requirement of neutrophils in the circulation, such as in acute infections, than the production of lactoferrin and HNL. The ratio between the content of either of the secondary granule proteins and MPO would therefore provide us with an estimate of the relative size of the various maturation stages of neutrophils in the blood and an indication of the bone marrow turnover of neutrophils.

Figure 2:
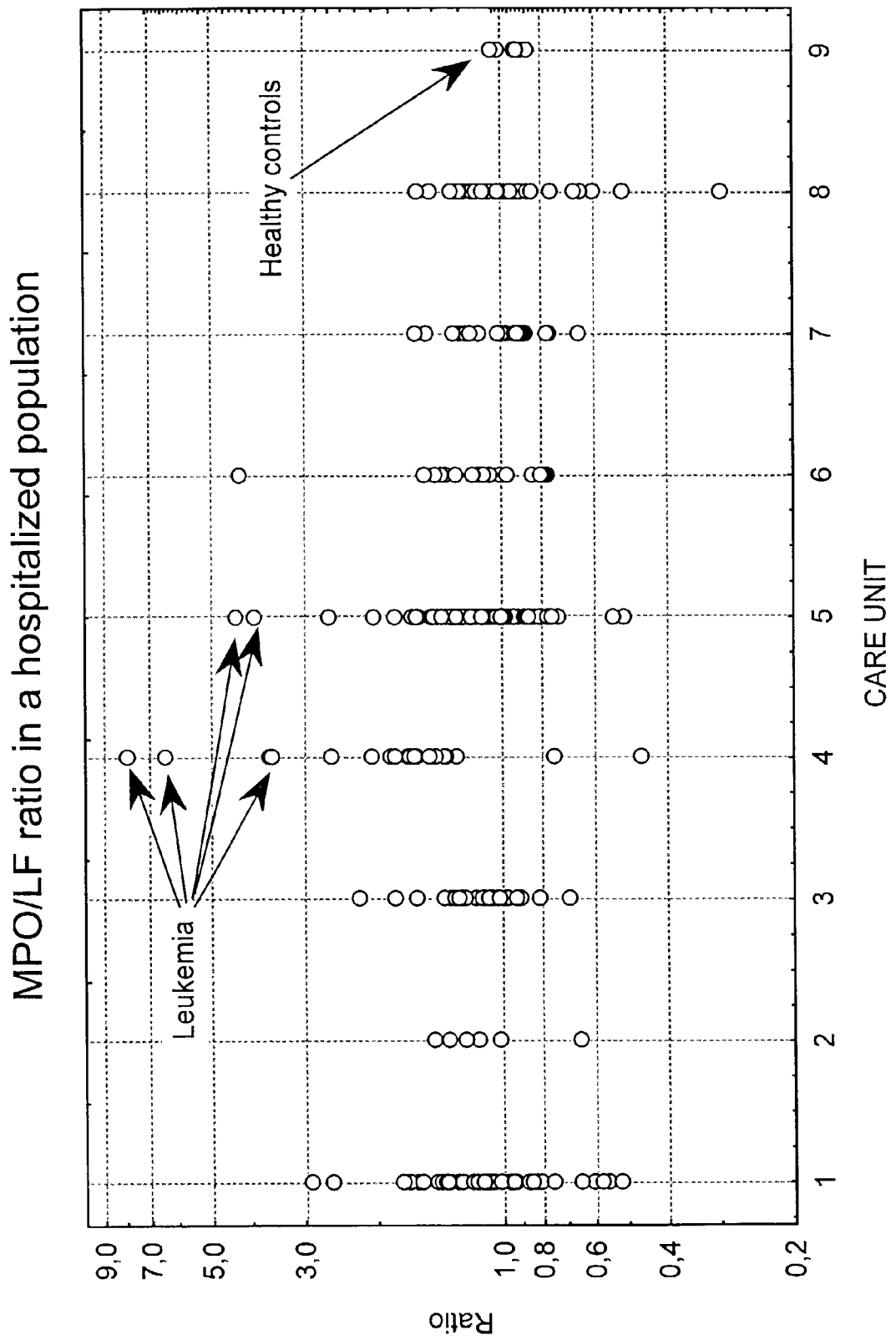
FIG. 2 shows ratio between MPO and lactoferrin in detergent extracted whole blood.

It is shown in FIG. 2 that a ratio between MPO concentration and lactoferrin concentration in extracted whole blood varies about 20-fold between patients, with myeloid leukemia patients having the highest ratios.

EXAMPLE 3

Estimation of the Number of Blood Eosinophils

In this example it is shown that extraction of a small aliquot of blood, 1-10 μl, with CTAB, 0.05-0.5%, for at least 1 minute and the subsequent measurement of the eosinophil protein EPO by means of a specific immunoassay accurately estimates the numbers of eosinophils in the blood.

Figure 3:
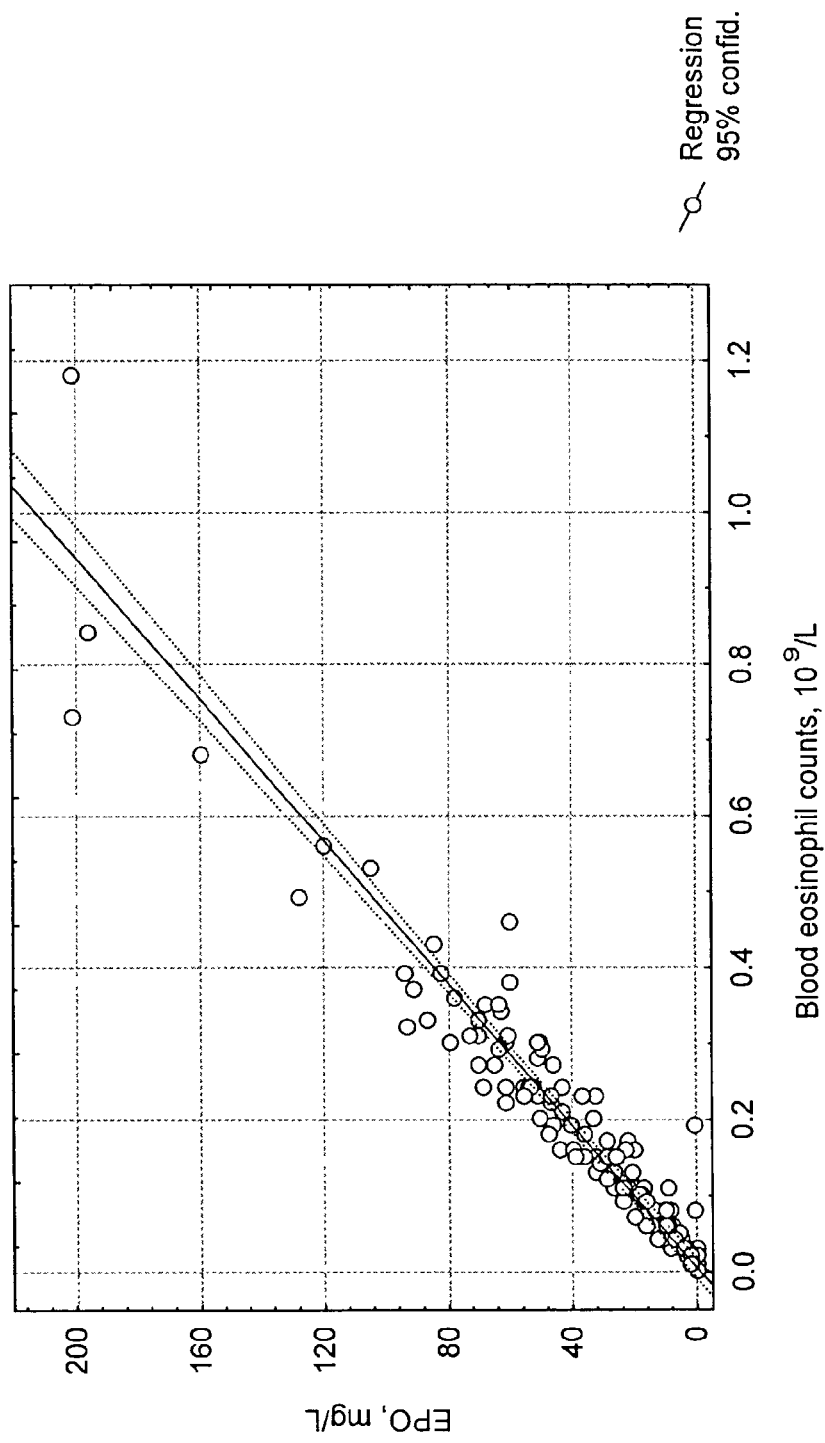
FIG. 3 shows a correlation between the number of eosinophils and the concentration of EPO protein in detergent extracted whole blood.

As shown in FIG. 3, the concentration of EPO in the extract was significantly and linearly correlated (r=0.95) to the number of eosinophils in the extracted blood as estimated by means of a Coulter STKS (Beckman Coulter, Inc.) cell counter. From the equation of the regression line it is apparent that the deviation from origo was minimal, indicating the cell specificity of the measurement. The results were obtained from a mixed population of hospitalized patients (n=275) having both elevated and reduced levels of eosinophils in the their blood. Thus, some patients had elevated numbers because of allergy and asthma, chronic inflammatory diseases, cancer etc. and some had reduced numbers because of, among other things, acute infections. In spite of the inclusion of these extremes in the calculation, the relationship between number of eosinophils and the concentration of EPO was linear over the entire range measured. When EPX was measured the corresponding correlation was r=0.93 and also with a linear relationship to the number of eosinophils over the entire range.

The above examples 1-3 describe neutrophils, different maturation forms of neutrophils, and eosinophils. However the invention is not to be construed as limited to these cell types.

For example the basophil protein BB1 may measure basophils.

Cell surface markers such as CD20 may measure B-lymphocytes and CD3 T-lymphocytes.

The cell surface markers CD4 and CD8 may be used to measure different lymphocyte populations.

Monocytes may be measured by CD14 or lysozyme.

Thrombocytes may be measured by β-tromboglobulin

Determination of ratios is especially interesting for myeloid cells as described in Example 2, but also for various subpopulations of lymphocytes.

REFERENCES

Agner K. Crystalline myeloperoxidase. Acta Chem Scand 1958; 12:89-94.

Borregaard N, Heiple JM, Simons ER et al. Subcellular localization of the b-cytochrome component of the human neutrophil microbicidal oxidase: translocation during activation. J. Cell. Biol. 1983;97:52-61

Carlson MGCh, Peterson CGB, Venge P. Human eosinophil peroxidase: Purification and characterization. J Immunol 1985; 134:1875-9.

Cooray R, Petersson CGB, Holmberg O. Isolation and purification of bovine myeloperoxidase from neutrophil granules. Vet Immunol Immunopathol 1993; 38:261-72.

Galfré G, Howe SC, Milstein C et al. Antibodies to major histocompatibility antigens produced by hybrid cell lines. Nature 1977;266:550-552

Klempner MS, Mikkelsen RB, Corfman DH et al. Neutrophil plasma membranes. I. High-yield purification of human neutrophil plasma membrane vesicles by nitrogen cavitation and differential centrifugation. et al., J Cell Biol July 1980;86(1):21-28.

Nielsen LP, Bjerke T, Christensen MB et al. Eosinophil markers in seasonal allergic rhinitis. Intranasal fluticasone propionate inhibits local and systemic increases during the pollen season. Allergy 1998; 53:778-85.

Olofsson T, Olsson I, Venge P et al. Serum myeloperoxidase and lactoferrin in neutropenia. Scand J Haematol 1977; 18(1):73-80.

Olsson I, Olofsson T, Odeberg H. Myeloperoxidase-mediated iodination in granulocytes. Scand J Haematol 1972; 9(5): 483-91.

Oucterlony Ö. Antigen antibody reactions in gels. Acta Pathol Microbiol Scand 1949;26:507.

Peterson CGB, Jörnvall H, Venge P. Purification and characterization of eosinophil cationic protein from normal human eosinophils. Eur J Haematol 1988; 40:415-23.

Peterson CGB, Venge P. Purification and characterization of a new cationic protein-eosinophil protein-X (EPX)—from granules of human eosinophils. Immunol 1983; 50:19-26.

Reiter B. The biological significance of lactoferrin. Int J Tissue React 1983; 5:87-96.

Xu SY, Carlson M, Engström et al. Purification and characterization of a human neutrophil lipocalin (HNL) from the secondary granules of human neutrophils. Scand J Clin Lab Invest 1994; 54:365-76.

Xu SY, Peterson CGB, Carlson M et al. The development of an assay for human neutrophil lipocalin (HNL)—to be used as a specific marker of neutrophil activity in vivo and vitro. J Immunol Methods 1994; 171:245-52.

The invention claimed is:

1. A method for in vitro estimating an amount of specific cells in a patient sample using cell specific molecules, the method comprising
  a) extracting cell specific molecules from cells contained in an aliquot of the patient sample;
  b) measuring the concentration of at least two cell specific molecules in the extracted aliquot by immunological assay; and c) estimating the amount of specific cells that contained the at least two cell-specific molecules from a ratio between the measured concentrations of the cell specific molecules.

2. The method according to claim 1, wherein the extraction is conducted with cationic detergent.

3. The method according to claim 2, wherein the detergent is CTAB (N-cetyl-N,N,N-trimethylammonium bromide).

4. The method according to claim 1, wherein the patient sample is whole blood.

5. The method according to claim 1, wherein the cell specific molecules are intracellular and extracellular proteins or cell surface markers.

6. The method according to claim 1, wherein the concentration of each cell specific molecule is correlated with a number of a subtype of cells.

7. The method according to claim 1, wherein the cell specific molecules comprise a neutrophil protein.

8. The method according to claim 7, wherein the neutrophil protein comprises MPO (myeloperoxidase), HNL (human neutrophil lipocalin) or lactoferrin.

9. The method according to claim 1, wherein the cell specific molecules comprise an eosinophil protein.

10. The method according to claim 9, wherein the eosinophil protein comprises EPX (eosinophil protein x) or EPO (eosinophil peroxidase).

11. The method according to claim 1, wherein the cell specific molecules comprise a basophil protein.

12. The method according to claim 11, wherein the basophil protein is BB1.

13. The method according to claim 1, wherein the cell specific molecules comprise a thrombocytic protein for measuring thrombocytes.

14. The method according to claim 13, wherein the thrombocytic protein is β-thromboglobulin.

15. The method according to claim 1, wherein the cell specific molecules comprise cell surface markers for measuring B-lymphocytes and CD3 T-lymphocytes.

16. The method according to claim 15, wherein the cell surface markers are CD20.

17. The method according to claim 1, wherein the cell specific molecules comprise cell surface markers for measuring different lymphocyte populations.

18. The method according to claim 17, wherein the cell surface markers are CD4 or CD8.

19. The method according to claim 1, wherein the cell specific molecules are CD14 or lysozyme for measuring monocytes.

20. The method according to claim 1, wherein the cell specific molecules comprise myeloperoxidase and lactoeffin.

* * * * *

UNITED STATES PATENT AND TRADEMARK OFFICE
CERTIFICATE OF CORRECTION

PATENT NO. : 7,405,047 B2  
APPLICATION NO. : 10/178211  
DATED : June 24, 2002  
INVENTOR(S) : Per Venge Page 1 of 1

It is certified that error appears in the above-identified patent and that said Letters Patent is hereby corrected as shown below:

Claim 20, column 8, line 24, change to "lactoeffin" to -- lactoferrin --.

Signed and Sealed this

Twenty-third Day of September, 2008

JON W. DUDAS  
*Director of the United States Patent and Trademark Office*

UNITED STATES PATENT AND TRADEMARK OFFICE
CERTIFICATE OF CORRECTION

PATENT NO.        : 7,405,047 B2
APPLICATION NO.  : 10/178211
DATED             : July 29, 2008
INVENTOR(S)       : Per Venge It is certified that error appears in the above-identified patent and that said Letters Patent is hereby corrected as shown below:

Claim 20, column 8, line 24, change to "lactoeffin" to -- lactoferrin --.

This certificate supersedes the Certificate of Correction issued September 23, 2008.

Signed and Sealed this

Fourteenth Day of October, 2008

JON W. DUDAS
*Director of the United States Patent and Trademark Office*